United States Patent [19]

Sitz et al.

[11] Patent Number: 5,278,336

[45] Date of Patent: Jan. 11, 1994

[54] PROCESS FOR EXCHANGING INHIBITOR(S) IN OLEFINICALLY UNSATURATED SYSTEMS WHICH ARE REACTIVE VIA FREE RADICALS

[75] Inventors: Hans-Dieter Sitz, Rommerskirchen; Wolfgang Ritter, Haan, both of Fed. Rep. of Germany

[73] Assignee: Henkel Kommanditgesellschaft auf Aktien, Duesseldorf, Fed. Rep. of Germany

[21] Appl. No.: 859,429

[22] PCT Filed: Nov. 19, 1990

[86] PCT No.: PCT/EP90/01976

§ 371 Date: Jul. 24, 1992

§ 102(e) Date: Jul. 24, 1992

[87] PCT Pub. No.: WO91/08192

PCT Pub. Date: Jun. 13, 1991

[30] Foreign Application Priority Data

Nov. 27, 1989 [DE] Fed. Rep. of Germany ....... 3939162

[51] Int. Cl.$^5$ .............................................. C07C 69/74
[52] U.S. Cl. ................................................... 560/218
[58] Field of Search ......................................... 560/218

[56] References Cited

U.S. PATENT DOCUMENTS 3,989,740 11/1976 Broussard et al. ................. 560/218

FOREIGN PATENT DOCUMENTS 2106052 5/1987 Japan .

*Primary Examiner*—Paul J. Killos
*Attorney, Agent, or Firm*—Wayne C. Jaeschke; John E. Drach; Henry E. Millson, Jr.

[57] ABSTRACT

The invention describes a process for the partial or complete exchange of the free radical inhibitors (preparation inhibitor) from their admixtures with free radical-reactive—and especially polymerizable and/or cross-linkable—olefinically mono- and/or polyunsaturated compounds against free radical inhibitors or inhibitor systems (application inhibitor), the kind and amount of which are freely determinable. The process according to the invention is characterized in that admixtures reactive via free radicals are employed which contain, as the preparation inhibitor, appropriate compounds of the phenol type comprising hydroxyl groups capable of forming salts, this feedstock mixture as a liquid phase is subjected to a treatment with solid oxides, carbonates and/or hydroxides of the alkali metals and/or alkaline earth metals, which may also be present in admixture with further oxidic metal compounds, thereby in a pre-determinable manner binding all or part of the preparation inhibitor to the solid phase, the resulting solid phase is separated from the liquid phase, and the content of the application inhibitor in this liquid phase is adjusted with respect to kind an amount thereof. The process is preferably applied to free radical-reactive substance mixtures, from which the preparation inhibitors contained therein cannot be satisfactorily removed by way of a distillation.

20 Claims, No Drawings

PROCESS FOR EXCHANGING INHIBITOR(S) IN OLEFINICALLY UNSATURATED SYSTEMS WHICH ARE REACTIVE VIA FREE RADICALS

BACKGROUND OF THE INVENTION

1. Field of the Invention

The invention describes a technical teaching which allows significant improvements to be achieved in the area of a controlled inhibition of olefinically unsaturated systems which are reactive via free radicals. More specifically, the invention intends to demonstrate a new approach which enables a deliberate pre-selection to be made of the kind and amount of the free radical-inhibitor(s) employed in said systems for stabilization and to ensure this possibility of a deliberate pre-selection even in cases where the technologies as hitherto known for attaining this object have failed to be successful.

2. Statement of Related Art

The concomitant use of inhibitors in the preparation, storage and processing of free radical-sensitive olefinically unsaturated compounds or systems is common chemical knowledge. The inhibitors or inhibitor systems are intended to prevent the initiation of a free radical-initiated reaction at an undesired time; on the other hand, if said systems are intended to be put into use, the inhibitor action will have to be overcome by a controlled initiation of said free radical-initiated reaction. Depending on the conditions of the production of the olefinically unsaturated compounds and/or of the corresponding systems, on the reactivity of the compounds or molecular moieties involved, on the conditions of storage and eventually on the given conditions of use, difficulties may be encounterd in meeting the broad profile of demands as set for stability control by free radical-inhibitors by means of just one special selected inhibitor or inhibitor system. Accordingly, there may be distinguished between "preparation inhibitors" and "application inhibitors" which may be unlike with respect to kind and/or quantity. Thus, for example, it may be desirable, in the preparation of the reactive systems to employ comparably strong inhibitors and/or comparably increased amounts of inhibitors (preparation inhibitors), whereas the storage and/or processing of the reactive system, then, will only require inhibitor or inhibitor systems (application inhibitors) that are comparably less active with respect to kind and/or quantity thereof. In numerous cases it is possible, comparably without any major problem to exchange the preparation inhibitors for the application inhibitors. As an example, there may be mentioned the distillative purification of substance mixtures containing comparably less volatile inhibitors in admixture with distillable olefinically unsaturated components, so that it will be possible, by means of a distillation to isolate the inhibitor-free olefinically unsaturated compound. The pure product thus recovered can then be admixed in a predeterminable manner with the application inhibitor.

Nevertheless, practice knows many cases wherein such an easy separation of the substance mixture as primarily obtained in the preparation and comprising the preparation inhibitor and the compound reactive via free radicals is not possible. This may be the case, for example, if a distillative separation of the inhibited substance mixture as primarily obtained cannot be effected, e.g. because the boiling points of the unsaturated components are too high or for other reasons. In these and in comparable cases, usually the preparation inhibitor necessarily will also become the application inhibitor. This linkage often causes undesirable bonds for the technology of the step of the preparation of the free radical-reactive system to the technological requirements of the system, including its inhibitor content in practical use.

DESCRIPTION OF THE INVENTION

It is the object of the invention to show a new approach to how such an undesirable bond can be resolved between the technologies governed by different laws of the involved steps with respect to the nature of the inhibitors as respectively present. Here, more particularly, the invention is intended to provide the possibility of independently pre-selecting the kind and amount of the application inhibitor in free radical-reactive systems of the type concerned here without having to regard the particularities in the preparation of the radical-sensitive systems. As a technical solution to this problem, the invention proposes the use, as preparation inhibitor, of a group of selected inhibitors which by way of a simple reaction with the auxiliary materials described hereinbelow can be bound and in this state can be removed from the system, then allowing the addition of application inhibitors by way of a free selection of the kind and/or amount thereof.

Accordingly, the invention relates to a process for the partial or complete exchange of the free radical inhibitors (preparation inhibitor) from their admixtures with free radical-reactive—and especially polymerizable and/or cross-linkable olefinically mono- and/or polyunsaturated compounds against free radical inhibitors or inhibitor systems (application inhibitor), the kind and amount of which are freely determinable; said process is characterized in that admixtures reactive via free radicals are employed which contain, as the preparation inhibitor, appropriate compounds of the phenol type comprising hydroxyl groups capable of forming salts, this feedstock mixture as a liquid phase is subjected to a treatment with solid oxides, carbonates and/or hydroxides of the alkali metals and/or alkaline earth metals, which may also be present in admixture with further oxidic metal compounds, thereby in a predeterminable manner binding all or part of the preparation inhibitor to the solid phase, the resulting solid phase is separated from the liquid phase, and the content of the application inhibitor in this liquid phase is adjusted with respect to kind an amount thereof.

Thus, the teaching of the invention resides on two essential elements As the preparation inhibitors there are provided selected compounds of this type possessing hydroxyl groups that are capable of undergoing salt formation. The removal thereof from the systems which are reactive via free radicals is made possible by the treatment with selected solid reactants to bind the preparation inhibitors to this solid phase, whereas the system to be inhibited is retained in the liquid phase. Then, the depletion and even complete removal of the preparation inhibitor from the feedstock mixture can be successfully achieved by means of a simple phase separation. The process according to the invention is particularly suitable for those free radical-reactive substance mixtures, from which the preparation inhibitors contained therein cannot be removed at all or satisfactorily by way of a distillation.

Phenol compounds containing free hydroxyl groups capable of undergoing salt formation are a class of compounds known in the art of polymerization for their marked inhibitor activity against a reaction initiation by free radicals. Particularly active representatives are found in the class of the hydroquinone compounds, especially the ring-substituted hydroquinone compounds.

It has been found that more or less significant differences exist in the respective substance-typical reactivity under the reaction conditions still to be discussed in greater detail hereinbelow for the reaction of such inhibitors of the phenol type or hydroquinone type with the solid oxides and/or hydroxides of the alkaline earth metals to form a salt and to bind the inhibitor to the precipitant employed as the solid phase. In particular, α-substituted hydroquinone compounds and among these dialkyl-substituted hydroquinones are especially reactive and, therefore, are especially suitable for the use as preparation inhibitor in the process according to the invention. This class of inhibitors is distinguished by a high inhibiting activity against an undesired free radical-initiated polymerization, so that an inhibiting activity against an undesired free radical-initiated reaction in the preparation phase can be adjusted such as to be satisfactory for the practical demands. Inhibitors having a particularly strong inhibiting effect, for example, are dialkyl-substituted hydroquinones and, among these, especially 2,5-di-tert.butyl hydroquinone which can be employed for stabilization in virtually any freely determinable amount in the step of the preparation of the reactive system. By way of the subsequent removal according to the invention of such salt-forming inhibitors through an at least partial binding thereof to a solid precipitant and subsequent phase separation it is made possible, to exchange the strong free radical-inhibiting preparation inhibitors, for example, according to kind and/or amount thereof against weaker free radical-inhibiting application inhibitors.

The principles underlying the invention are described hereinbelow by way of using a selected substance class as example, where the concomitant use of the measures proposed according to the invention is of particular interest. Nevertheless, the artisan will immediately understand that the scope of the field of where the invention can be applied is not limited to this specific substance class. The working procedures as newly proposed are usable in any optional case of applications responding to technologically caused or freely selected problems.

Low-volatile polyfunctional esters of acrylic acid and/or methacrylic acid with polyfunctional alcohols—herebelow also designated as (meth)acrylic acid esters or poly(meth)acrylic acid esters, respectively—are known to be prepared by the catalytic reaction of the reactants with the addition of polymerization inhibitors to the reaction mixture. (Meth)Acrylic acid esters of this kind have gained increasing importance as highly reactive components in, for example, radiation-curable systems. The polyfunctional alcohols involved here are, for example, di- to tetrahydric aliphatic saturated alcohols and/or the oxalkylation products thereof. Polyfunctional (meth)acrylic acid esters of the kind mentioned may be used, for example, as lacquer raw materials for electron beam curing or as a constituent of UV light-curing printing inks or corresponding coating compositions, in putty, molding or casting compositions as well as in adhesives, especially in anaerobically setting adhesives. Due to the comparably high reactivity of said materials, a concomitant use of inhibitors is required which, depending on the nature and/or amount used thereof, ensure a safe inhibition of the system subjected to esterification, even in the absence of an inert solvent, if the reaction is to be conducted in substance. It will be readily understood that here the preparation inhibitor will have to meet high demands.

However, the practical utilization of such low-volatile systems which cannot be purified by distillation may then be impaired by the strong inhibitor action as required during the preparation. The invention provides the possibility of eliminating this application-technological impairment.

Another readily intelligible case for using the process according to the invention will be constituted, if the intended use of the reactive systems will go beyond the limits of merely technical and/or technological considerations. This is always applicable, if the reactive systems to be applied need to be examined with respect to the physiological compatibility thereof, for example in the area of the technology of adhesive agents for use in the living organism. Here, highly active inhibitors of the kind of 2,5-di-tert.butyl hydroquinone would not be the first choice on the ground of physiological considerations. There is a demand for adhesives or adhesive systems containing inhibitors exhibiting a better physiological compatibility. According to the invention, such an exchange of preparation inhibitors having a limited physiological compatibility for application inhibitors having an improved physiological compatibility becomes possible. Here, a particularly suitable inhibitor is vitamin E, the use of which for purposes of the kind mentioned here is in detail described in the parallel patent application WO91/0799.

Of particular importance is the use of finely divided, especially finely powdered, oxides and/or hydroxides of calcium and/or magnesium for binding the preparation inhibitor. Among these two alkaline earth metals, the respective calcium compounds are of special importance. In a preferred embodiment of the invention, finely divided solids which at least portionwise contain calcium compounds of the kind mentioned are introduced into the step of inhibitor-binding. An especially important embodiment makes use of calcium hydroxide $Ca(OH)_2$ and/or burnt lime CaO. It is especially finely divided calcium hydroxide that frequently accomplishes the optimum removal of the preparation inhibitor from the reaction mixture.

By way of an optimization of the process parameters in the step of binding the preparation inhibitor, it is possible to remove the undesired inhibitor or undesired excess amounts of the inhibitor to a pre-determinable extent. The solids systems selected according to the invention and based on the oxides and/or hydroxides of the alkaline earth metals, and especially of magnesium and/or calcium, may lead to the initiation of an anionic polymerization and, hence, to a gelling of the reaction product, in comparably highly reactive olefinically unsaturated systems within the range of room temperature or also still at slightly elevated temperatures. Thus, according to the invention it is preferred to carry out the process of binding the preparation inhibitor at temperatures above 50° C.; the temperature range of from about 60° C. to 110° C. has proven to be an especially interesting range, with the range of from about 70° C. to 90° C. being preferred. At temperatures of this working range, the salt-forming inhibitor binding is preferred over anionic polymerization initiation.

For reasons of economy, but also for reasons of providing an optimum protection of the per se unstable reaction mixture, the solid basic reaction aid is preferably employed only in a restricted stoichiometric excess. Thus, the residence time of the solid material suspended in the liquid feedstock material must be selected to be sufficient to ensure the desired contact between the solid and the liquid or dissolved inhibitors. In addition, the outer surface of the individual solid particle becomes occupied by the respectively formed salt. Thus, any deeper penetration of the reactive components to the core of the solid particle is hindered.

The duration of the treatment of liquid reactive phase containing a preparation inhibitor for at least partially binding the inhibitor according to the invention may be carried out for a period of time extending over some hours, for example up to 5 hours, and preferably up to 3 hours. For an optimization of the process according to the invention, however, it may be desirable to adjust both process temperature and process time to each other in such a manner that the desired lower contents of the preparation inhibitor can be obtained with a duration of the treatment of less than 1 hour and especially of less than 45 minutes. In particularly preferred embodiments, the working conditions are adjusted so that the desired residual contents of the preparation inhibitor will have been attained within a period of up to about 30 minutes. If calcium hydroxide is employed, optimal values for the treatment can be a temperature of around 80° C. and a treatment duration of from about 10 to 30 minutes.

It has further been found that the presence of water in the feedstock material to be treated can be disadvantageous. Even comparably low amounts of aqueous solutions of bases of the kind as here involved obviously exert a stronger action on the feedstock material than the solid treatment agent used according to the invention in the dry state does. Thus, according to the invention it is first preferred that the material to be employed as the liquid phase from which the inhibitor is to be at least partially removed is at least largely free from water. Residual amounts of water pesent in the feedstock to be purified may be removed in a per se known manner, for example by azeotropic distillation with a concomitant use of auxiliary solvents, or simply by applying a vacuum for a sufficiently long time.

The quantity of the finely powdered basic auxiliary material is primarily determined by the portions of the preparation inhibitor to be altogether removed from the crude product. It is preferred to employ a stoichiometric excess of the finely powdered auxiliary material. It may usually be convenient to employ a limited excess of this solid auxiliary material within a range of up to 10 times the amount as stoichiometrically required, preferably with amounts up to 5 times the amount as stoichiometrically required. But also working with a comparably restricted excess, e.g. within the range of from at least about 1.3 times to about 3 times the amount as stoichiometrically required can be suitable.

Reactive compositions of the kind as concerned here —as will be evident from the following examples—often are esters or comparable reaction products which are characterized by containing residual amounts of catalysts, especially acidic catalysts, residual acids from the synthesis and like contaminations. Then the treatment according to the invention with the basic solids of the type described simultaneously can result in the partial or complete removal of such acidic portions to the effect of a dry neutralization. Details of the dry neutralization in the liquid phase of substance systems reactive via free radicals with the solid, preferably finely divided oxides and/or hydroxides of the alkaline earth metals which may also be present in admixture with further oxidic metal compounds are described in Applicants' parallel application Ser. No. 07/720,444 filed 23 Aug. 1991, now U.S. Pat. No. 5,210,281 ("Improved dry neutralization process for organic liquid phases"). Therein the teaching is described of that for the recovery of pure products, which even without a distillation have low residual acid values along with low color values, the neutralization is carried out with solid finely powdered oxides and/or hydroxides of the alkaline earth metals and thereafter the organic liquid phase is separated from the finely powdered solid phase. Thereby, under the working conditions as detailed in said parallel Patent Application, it is successfully accomplished to obtain optimized product properties and especially to combine low residual acid values with low color values. The teaching of the present invention relates to the combination of said purification measures with the partial or complete removal of the preparation inhibitors from these reaction compositions, which is the main goal of the present invention. More specifically, in this embodiment one additional aspect deserves to be particularly mentioned: It has proven to be useful to carry out the reaction of the liquid material to be purified with the finely powdered basic solid mass at least partially under a reduced pressure, even if the liquid starting material to be neutralized and to be freed from the preparation inhibitor is per se anhydrous. In the operation under reduced pressure, also the amount of water formed in the course of the neutralization is withdrawn from the reaction mixture and, thus, an in situ formation of aqueous-basic portions of the solution upon neutralization is prevented or at least restricted. Here it may be useful to conduct the treatment within the pressure range of from 1 to 150 mbar, e g at from about 20 to 150 mbar, while working within the range of from about 20 to 100 mbar may be particularly preferred. In this way it is possible, to successfully reduce the residual water levels in the final product to values of less than about 0.1% by weight, whereas upon the dry treatment of crude products as common in practice due to the contents thereof of free acid components—especially catalysts, residual acids and the like—after the completion of the treatment without an application of vacuum the residual water levels may be within the range of from about 0.7 to 0.9% by weight. It has been found that alone these higher amounts of residual water may cause a substantial deterioration in the color value of the purified final product.

As has already been stated, the oxidic and/or hydroxidic alkaline earth metal compounds may also be employed in admixture with further basic metal oxides or metal oxide compounds capable of undergoing salt formation. Here, a particularly interesting example is hydrotalcite. Combinations of hydrotalcite and basic calcium compounds result in a particularly good combination of the desired values in the final product. As to the nature of hydrotalcite which occurs as a natural product and/or can be synthesized, reference is made to the pertinent literature; hereto cf., e.g., R. Allmann et al., "Die Struktur des Hydrotalkits", N. Jahrb. Mineral. Monatsh. 1969, 544–561.

Then, as the application inhibitors there may be added inhibitor systems or individual inhibitor components that are freely chosen with respect to kind and amount thereof and are tailored to meet the particular requirements with respect to storage and use of the purified reactive compositions. As has already been set forth, one important embodiment may be constituted by employing the purification treatment according to the invention to exchange the strong radical-inhibiting preparation inhibitors with respect to kind and amount thereof for the application inhibitors having a weaker inhibiting action or to exchange preparation inhibitors of poor physiological compatibility for better compatible application inhibitors.

From the comprehensive literature on the importance, nature and selection of inhibitors and inhibitor systems of the kind concerned here, which may find use as application inhibitors, reference is made, for example, to Polymer Handbook, Second Edition, JOHN WILEY & SONS, New York 1979. Volume II, pp. 53–55; and to Enzyc. Polym. Sci. Technol. 1967, Volume 7, pp. 644–664.

EXAMPLE 1

In a 1 liter-flask there was placed a weighed amount of 800 g of a crude esterification product—consisting of 28 g of toluenesulfonic acid, 1.6 g of 2,5-di-tert.-butylhydroquinone, 0.8 g of hydroquinone, 30.8 g of acrylic acid and 740.6 g of trimethylolpropane +3 EO triacrylate - . The crude product was neutralized at a temperature of 80° C. with stirring and passing air through the mixture in an amount of 10 l/h. For the neutralization there was employed two times the equivalent amount of base, relative to the acid value of the crude product (acid value: 40 mg of KOH per 1 g of substance).

After 1, 2 and 3 hours 260 g each of the neutralized product were taken out and filtered by means of a pressurized nutsch filter. The results reporting the inhibitor contents and the acid values are summarized in Table 1.

TABLE 1

Inhibitor contents as dependent on the neutralizing agent and the neutralizing time employed

| Initial product: | Trimethylolpropane + 3 EO triacrylate | | | |
|---|---|---|---|---|
| Acid value: | 40 mg KOH per gram | | | |
| Inhibitors: | 2,000 ppm of 2,5-Di-tert.-butylhydroquinone (DTBHQ); | | | |
| | 1,000 ppm of Hydroquinone (HQ). | | | |
| Temperature: 80° C. | Neutralization Time minutes | Inhibitor DTBHQ ppm | Contents HQ pm | Acid Value mg of KOH/g |
| LiOH | 60 | 1,000 | 820 | 9.8 |
| (2 equivalents) | 120 | 0 | 740 | 2.2 |
| | 180 | 0 | 670 | 1.3 |
| NaOH | 60 | 1,000 | 770 | 25.8 |
| (finely powdered) | 120 | 0 | 750 | 5.0 |
| (2 equivalents) | 180 | 0 | 720 | 2.8 |
| Ca(OH)$_2$ | 60 | 0 | 670 | 0.9 |
| (2 equivalents) | 120 | 0 | 590 | 0.2 |
| | 180 | 0 | 540 | 0.1 |
| MgO | 60 | 890 | 930 | 5.8 |
| (2 equivalents) | 120 | 850 | 930 | 5.6 |
| | 180 | 820 | 930 | 3.1 |
| CaO | 60 | 1,180 | 980 | 23.6 |
| (2 equivalents) | 120 | 890 | 960 | 8.4 |
| | 180 | 0 | 950 | 3.2 |

EXAMPLE 2

In a 2 liter-flask there was placed a weighed amount of 1.0 kg of an esterification product (35 g of p-toluenesulfonic acid, 2 g of 2,5-di-tert.-butylhydroquinone, 35.9 g of acrylic acid, 927.1 g of trimethylolpropane +3 EO triacrylate; acid value: 38 mg of KOH per 1 g of substance); the product was neutralized at a temperature of 80° C. and under a pressure of 50 mbar with passing air through the mixture in an amount of 20 l/h. The neutralizing agents employed were Ca(OH)$_2$, CaO and combinations comprising weaker and stronger basic substances.

| Ca(OH)$_2$: | 49.9 g | (2 equivalents) |
|---|---|---|
| CaO: | 37.8 g | (2 equivalents) |
| Mixtures: (1:1 equivalents) | | |
| a) | 10.2 g of MgO | (1.5 equivalents |
| | 18.7 g of Ca(OH)$_2$ | relative to the acid value of the crude product) |
| b) | 17.8 g of hydrotalcite | (1.5 equivalents, |
| | 19.7 g of Ca(OH)$_2$ | relative to the acid value of the crude product) |
| Combinations: | | |
| a) | 28.5 g of MgO | 60 minutes (2 equivalents, relative to the acid value of the crude product) |
| | +20.1 g of Ca(OH)$_2$ | 120 minutes (1.5 equivalents, relative to the acid value after 60 minutes); |
| b) | 47.5 g of hydrotalcite | 60 min. (2 equivalents, relative to the acid value of the crude product) |
| | +8.0 g of Ca(OH)$_2$ | 120 minutes (1.5 equivalents, relative to the acid value after 60 minutes). |

One third each of the total amount of the product was taken out after 60, 120 and 180 minutes and filtered by means of a pressurized nutsch filter. The results reporting the inhibitor contents, the acid values and the color values are summarized in Table 2.

TABLE 2

Inhibitor contents as dependent on the neutralizing agent and the neutralizing time employed

| Initial product: | Trimethylolpropane + 3 EO triacrylate | | | |
|---|---|---|---|---|
| Acid value: | 38 mg KOH per gram | | | |
| Inhibitor: | 1,920 ppm of 2,5-Di-tert.-butylhydroquinone (DTBHQ). | | | |
| Temperature 80° C. Pressure: 50 mbar | Neutralization Time minutes | DTBHQ ppm | Acid Value mg of KOH/g | Gardner Color Value |
| 49.9 g of Ca(OH)$_2$ | 60 | <10 | 0 | <1 |
| (2 equivalents) | 120 | <10 | 0 | 2 |
| | 180 | <10 | 0 | 3 |
| 37.8 g of CaO | 60 | 1,050 | 3.9 | <1 |
| (2 equivalents) | 120 | 750 | 1.7 | 1-2 |
| | 180 | <10 | 0.1 | 1-2 |
| Combination | | | | |
| 27.2 g of MgO | 60 | 1,860 | 15.7 | <1 |
| (2 equivalents, | 120 | 1,450 | 8.1 | <1 |
| relative to the acid value) | | | | |
| +15.5 g of Ca(OH)$_2$ | 180 | 1,200 | 7.1 | <1 |
| (1.5 equivalents, relative to the acid value after 60 minutes | | | | |
| Combination | | | | |
| 45.2 g of hydrotalcite | 60 | 850 | 14.1 | <1 |
| (2 equivalents, | 120 | 810 | 5.5 | 1 |
| relative to the acid value) | | | | |
| +14.0 g of Ca(OH)$_2$ | 180 | 800 | 4.8 | 1 |
| (1.5 equivalents, relative to the acid value after 60 minutes | | | | |

TABLE 2-continued

Inhibitor contents as dependent on the neutralizing agent and the neutralizing time employed

| Initial product: | Trimethylolpropane + 3 EO triacrylate |
| --- | --- |
| Acid value: | 38 mg KOH per gram |
| Inhibitor: | 1,920 ppm of 2,5-Di-tert.-butylhydroquinone (DTBHQ). |

| Temperature 80° C. Pressure: 50 mbar | Neutralization Time minutes | DTBHQ ppm | Acid Value mg of KOH/g | Gardner Color Value |
| --- | --- | --- | --- | --- |
| Mixture: (1:1 equivalents) | | | | |
| 18.7 g of Ca(OH)$_2$ | 60 | 470 | 3.4 | <1 |
| 10.2 g of MgO | 120 | 160 | 3.1 | <1 |
| (1.5 equivalents) | 180 | 160 | 2.6 | <1 |
| Mixture (1:1 equivalents) | | | | |
| 18.7 g of Ca(OH)$_2$ | 60 | 1,370 | 7.8 | <1 |
| 17.0 g of hydrotalcite | 120 | 970 | 3.4 | 1 |
| (1.5 equivalents) | 180 | 690 | 1.8 | 1 |

EXAMPLE 3

In a 2 liter-reactor there was placed a weighed amount of 1.0 kg of an esterification product (35 g of p-toluenesulfonic acid, 1.81 g of 2,5-di-tert.-butyl-hydroquinone, 38.5 g of acrylic acid, 924.7 g of neopentyl glycol +2 PO diacrylate; acid value: 40 mg of KOH per 1 g of substance); the product was neutralized at a temperature of 80° C. and under a pressure of 50 mbar with passing air through the mixture in an amount of 20 l/h. The amounts used of the neutralizing agents were Ca(OH)$_2$: 26.2 g; 39.9 g; 52.4 g;
CaO: 19.9 g; 29.8 g; 39.7 g.

After neutralization times of 1, 2 and 3 hours, one third each of the total amount of the product was taken out and filtered by means of a pressurized nutsch filter. The results reporting the acid values, the inhibitor contents and the color values are summarized in Table 3.

TABLE 3

Inhibitor contents as dependent on the amounts of neutralizing agent and the neutralizing time employed

| Initial product: | Neopentyl glycol + 3 PO diacrylate |
| --- | --- |
| Acid value: | 40 mg KOH per gram |
| Inhibitor: | 1,810 ppm of 2,5-Di-tert.-butylhydroquinone (DTBHQ). |
| Gardner color value: | 1. |

| Temperature: 80° C. Pressure: 50 mbar | Neutralization Time hours | DTBHQ ppm | Acid Value mg of KOH/g | Gardner Color Value |
| --- | --- | --- | --- | --- |
| 26.2 g of Ca(OH)$_2$ | 1 | 1,020 | 9.2 | <1 |
| (1 equivalent) | 2 | 830 | 6.7 | <1 |
|  | 3 | 770 | 5.7 | <1 |
| 39.3 g of Ca(OH)$_2$ | 1 | 890 | 3.6 | <1 |
| (1.5 equivalents) | 2 | 680 | 2.5 | <1 |
|  | 3 | 600 | 1.8 | <1 |
| 52.4 g of Ca(OH)$_2$ | 1 | <20 | 0.2 | <1 |
| (2 equivalents) | 2 | <20 | 0 | 2 |
|  | 3 | <20 | 0 | 3 |
| 19.9 g of CaO | 1 | 1,810 | 15.7 | <1 |
| (1 equivalent) | 2 | 1,450 | 8.1 | <1 |
|  | 3 | 1,200 | 7.1 | <1 |
| 29.8 g of CaO | 1 | 1,440 | 11.4 | <1 |
| (1.5 equivalents) | 2 | 1,210 | 6.5 | <1 |
|  | 3 | 940 | 4.8 | <1 |
| 39.7 g of CaO | 1 | 1,490 | 5.6 | <1 |
| (2 equivalents) | 2 | 1,200 | 2.6 | <1 |
|  | 3 | 890 | 1.6 | <1 |

EXAMPLE 4

In a 2 liter-reactor there was placed a weighed amount of 1.8 kg of an esterification product (same as in Example 2), and the product was neutralized at a temperature of 80° C. and under a pressure of 50 mbar with passing air through the mixture in an amount of 20 l/h.

After periods of 10, 20, 30, 40, 50, 60, 120, 180 and 1 440 minutes, quantities of about 200 g each were taken out and filtered by means of a pressurized nutsch filter. The results reporting the acid values, the inhibitor contents and the color values are summarized in Table 4.

TABLE 4

Inhibitor contents as dependent on the neutralizing agent and the neutralizing time employed

| Initial product: | Trimethylolpropane + 3 EO triacrylate |
| --- | --- |
| Acid value: | 38 mg KOH per gram |
| Inhibitor: | 1,920 ppm of 2,5-Di-tert.-butylhydroquinone (DTBHQ). |
| Gardner color value: | 1. |

| Temperature 80° C. Pressure: 50 mbar | Neutralization Time minutes | DTBHQ ppm | Acid Value mg of KOH/g | Gardner Color Value |
| --- | --- | --- | --- | --- |
| 90.3 g of Ca(OH)$_2$ | 10 | 830 | 0.3 | <1 |
| (2 equivalents) | 20 | 610 | 0 | <1 |
|  | 30 | 200 | 0 | <1 |
|  | 40 | <10 | 0 | <1 |
|  | 50 | <10 | 0 | 1 |
|  | 60 | <10 | 0 | 1 |
|  | 120 | <10 | 0 | 2 |
|  | 180 | <10 | 0 | 3 |
|  | 1440 | <10 | 0 | 4 |

What is claimed is:

1. A process for the removal of at least a portion of a free radical preparation inhibitor which is at least one phenol compound containing at least one free hydroxyl group capable of undergoing salt formation from a substantially anhydrous liquid mixture comprised of said preparation inhibitor, one or more polymerizable or cross-linkable olefinically mono-or polyunsaturated compounds and one or more application inhibitors comprising contacting said mixture with a solid phase which is comprised of alkali metal or alkaline earth metal carbonates, oxides, or hydroxides or combinations thereof to remove at least a portion of said preparation inhibitor thereby increasing the relative concentration of said application inhibitor in said liquid mixture.

2. The process of claim 1, wherein said preparation inhibitor is an α-substituted hydroquinone.

3. The process of claim 2 wherein said α-substituted hydroquinone is 2,5-di-tert-butylhydroquinone.

4. The process of claim 1 wherein said application inhibitor is vitamin E.

5. The process of claim 1 wherein said polymerizable or cross-linkable olefinically mono- or polyunsaturated compound is a methacrylate ester of a polyhydric alcohol.

6. The process of claim 5 wherein said polyhydric alcohol is a dihydric alcohol.

7. The process of claim 5 wherein said polyhydric alcohol is a tetrahydric alcohol.

8. The process of claim 1 wherein said solid phase is comprised of calcium hydroxide, magnesium hydroxide, or a combination thereof.

9. The process of claim 1 wherein said process is carried out in a temperature range of from about 60° C. to about 110° C.

10. The process of claim 9 wherein said temperature range is from about 70° C. to about 90° C.

11. The process of claim 1 wherein said process is carried out for a time period of no longer than about 3 hours.

12. The process of claim 11 wherein said time period is from about 5 to about 1 hour.

13. The process of claim 1 wherein said process is carried out in a pressure range of from about 1 to about 150 mbar.

14. The process of claim 1 wherein said solid phase is present in a range of from about 1.3 to 2.5 times the stoichiometric amount required to remove said preparation inhibitor.

15. A process for the substantially complete removal of a free radical preparation inhibitor which is at least one phenol compound containing at least one free hydroxyl group capable of undergoing salt formation from a substantially anhydrous liquid mixture comprised of said preparation inhibitor, one or more polymerizable or cross-linkable olefinically mono-or polyunsaturated compounds and one or more application inhibitors comprising contacting said mixture with dry powdery calcium hydroxide to substantially completely remove said preparation inhibitor thereby increasing the relative concentration of said application inhibitor in said liquid mixture.

16. A process for the removal of at least a portion of a free radical preparation inhibitor, which is at least one phenol compound containing at least one free hydroxyl group capable of undergoing salt formation, from a substantially anhydrous liquid mixture comprised of said preparation inhibitor and one or more polymerizable or cross-linkable olefinically mono- or polyunsaturated compounds, comprising the steps of:

A) contacting the liquid mixture with a solid phase comprised of alkali metal or alkaline earth metal carbonates, oxides, or hydroxides, or combinations thereof to bind at least a portion of said preparation inhibitor to the surfaces of the solid phase; and B) removing the solid phase containing bound preparation inhibitor from contact with the liquid phase.

17. The process of claim 16 wherein following step B) one or more application inhibitors are added to the liquid phase.

18. The process of claim 16 wherein step A) is carried out at a temperature in the range of from about 60° C. to about 110° C.

19. The process of claim 18 wherein step A) is carried out in a pressure range of from about 1 to about 150 mbar.

20. The process of claim 16 wherein said polymerizable or cross-linkable olefinically mono- or polyunsaturated compound is a methacrylate ester of a polyhydric alcohol.

* * * * *